United States Patent
Schomaker et al.

(10) Patent No.: US 9,745,250 B2
(45) Date of Patent: Aug. 29, 2017

(54) PROCESS TO CRYSTALLIZE CHELATING AGENTS

(71) Applicant: Akzo Nobel Chemicals International B.V., Arnhem (NL)

(72) Inventors: Elwin Schomaker, Arnhem (NL); Paulus Johannes Cornelis Van Haeren, Doetinchem (NL); Martin Heus, Arnhem (NL)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 15/309,516

(22) PCT Filed: May 11, 2015

(86) PCT No.: PCT/EP2015/060272
§ 371 (c)(1),
(2) Date: Nov. 8, 2016

(87) PCT Pub. No.: WO2015/173157
PCT Pub. Date: Nov. 19, 2015

(65) Prior Publication Data
US 2017/0158613 A1    Jun. 8, 2017

(30) Foreign Application Priority Data

May 13, 2014 (EP) .................................... 14168184

(51) Int. Cl.
*C07C 227/00* (2006.01)
*C07C 227/42* (2006.01)

(52) U.S. Cl.
CPC .................................. *C07C 227/42* (2013.01)

(58) Field of Classification Search
CPC .................................................. C07C 227/42
See application file for complete search history.

(56) References Cited

U.S. PATENT DOCUMENTS

| | | |
|---|---|---|
| 5,981,798 A | 11/1999 | Schönherr et al. |
| 2012/0046491 A1 | 2/2012 | Mrzena et al. |
| 2012/0149936 A1 | 6/2012 | Baranyai |
| 2015/0321995 A1 | 11/2015 | Van Lare et al. |
| 2015/0353475 A1 | 12/2015 | Doppen et al. |

FOREIGN PATENT DOCUMENTS

| | | |
|---|---|---|
| CN | 201832438 U | 5/2011 |
| DE | 42 11 713 A1 | 10/1993 |
| EP | 2 277 855 A1 | 1/2011 |
| JP | 2002088037 A | 3/2002 |
| WO | 03/090721 A2 | 11/2003 |
| WO | 03/090786 A1 | 11/2003 |
| WO | 03/091272 A1 | 11/2003 |
| WO | 03/092852 A1 | 11/2003 |
| WO | 03/095059 A1 | 11/2003 |
| WO | 2008/065109 A1 | 6/2008 |
| WO | 2013/096122 A1 | 6/2013 |

OTHER PUBLICATIONS

European Search Report for EP Serial No. 14168184.1 dated Oct. 27, 2014.
International Search Report and Written Opinion for PCT/EP2015/060272 date of mailing Nov. 12, 2015.

*Primary Examiner* — Yevegeny Valenrod
*Assistant Examiner* — Blaine G Doletski
(74) *Attorney, Agent, or Firm* — Sandra B. Weiss

(57) ABSTRACT

The present invention relates to a process to crystallize a chelating agent containing a step of adding seeds to a saturated or supersaturated aqueous solution or dispersion of the chelating agent and a subsequent step of milling the dispersion, wherein the step of milling the dispersion is performed using equipment operating at at least 1,000 rpm, and to products obtainable by such process.

9 Claims, No Drawings

PROCESS TO CRYSTALLIZE CHELATING AGENTS

This application is a national stage filing under 35 U.S.C. §371 of PCT/EP2015/060272, filed May 11, 2015, which claims priority to European Patent Application No. 14168184.1, filed May 13, 2014, the contents of which are each incorporated herein by reference in their entireties.

The present invention relates to a process to crystallize chelating agents.

The detergent market is currently undergoing important changes. Due to ecological and regulatory reasons the use of phosphate in high concentrations in detergent formulations is to be banned altogether or must at least be greatly reduced. The formulators of detergent products have to find alternatives to replace the phosphate compounds, with the most promising replacements being the more easily biodegradable chelating agents, such as aspartic acid N,N diacetic acid and it salts (ASDA), methylglycine N,N-diacetic acid and its salts (MGDA) and glutamic acid N,N-diacetic acid and its salts (GLDA). Such chelating agents tend to be readily available and are used in a concentration from 5% to 60%. Many detergent formulations contain co-builders, which are typically polymers or phosphonates and also phosphates, silicates and zeolites. These co-builders are present in formulations in a concentration from 1% to 50%.

In powder or tablet detergent formulations, solid raw materials are required by the formulator. For example, in automatic dishwashing (ADW) applications the raw materials have to be in powder, and preferably granule, form to improve the tabletting and solids handling of the formulation. Powders or granules typically have a size comprised between 50 and 3,000 microns. However, the powder or granules of many chelating agents, when obtained in the amorphous state, show hygroscopic properties, which is unacceptable for the ADW formulators. The hygroscopic properties render the material sticky, thus introducing storage, handling and manufacturing problems. Flow properties of particles are critical in many ways. During manufacture of the particles themselves, they must flow smoothly relative to one another. Additionally, they must then be successfully transported to storage and transport containers. Finally, they must again be transported from storage and fed into a powder or tablet manufacturing facility. Flow problems arise due to several causes. In the case of amorphous chelating agents and their salts, poor flow will be caused by moisture pick-up, resulting in a wet sticky product that will form lumps. One way of avoiding hygroscopic properties is to work with chelating agents in their crystalline form.

US20120046491 discloses the preparation of a powder comprising one or more derivatives of glutamine-N,N-diacetic acid or glycine-N,N-diacetic acid with a degree of crystallinity of 30%, the process comprising concentrating an aqueous solution to obtain a crystal slurry, wherein one concentration range is from 20% to 60% by weight (starting material), based on the total weight of the crystal slurry, and ripening the crystal slurry in a paste bunker and then in a thin-film contact dryer, wherein the residence time in the paste bunker (seeds: fine powder up to 50% of total weight) and in the thin-film contact dryer is in total 15 minutes and the concentration occurs in an evaporator with rotating internals which are arranged at a distance relative to an inside wall of the evaporator of 1% of the diameter of the evaporator (high shear rate in the liquid film on the inside wall). Temperature ranges for the first process step are between 50° C.-140° C. and preferably between 80° C.-110° C., and pressure ranges are between 0.1 and 4 bar, preferably between 0.8 and 1.2 bar. Ripening is carried out for at least 15 minutes and up to 3 hours and thin-film treatment is carried out for between 0.5 minutes and 20 minutes from 60° C. up to 140° C. A powder is obtained which predominantly has the crystal modification of the monohydrate or the dihydrate of MGDA (methylglycine diacetic acid). The complicated process appears to be specifically designed for trisodium MGDA.

US20120149936 discloses a process for preparing crystalline solids of glycine-N,N-diacetic acid derivatives of sufficiently low hygroscopicity by introducing one crystalline compound as a seed; a spray granulation is carried out, which may be followed by a heat treatment step to increase the crystallinity. Only glycine-N,N-diacetic acid derivatives are mentioned in the document.

DE 42 11 713 discloses a process to prepare the chelating agents GLDA and ASDA (aspartic acid N,N-diacetic acid). Though it is suggested in general that the materials could be isolated by several methods, one of which is crystallization, all the examples deal with depositing ASDA in the amorphous form.

U.S. Pat. No. 5,981,798 discloses the preparation of a crystalline solid of a glycine N—N-diacetic acid derivative. In the Examples a concentrated solution of the trisodium salt of MGDA (methylglycine N,N-diacetic acid) is crystallized using seeds as crystallization initiator. In this document the glycine N,N diacetic acid derivatives, such as the trisodium salt of MGDA, are crystallized under mechanical stress. In the examples it is shown that such mechanical stress, said to come from a mixing, stirring, kneading or extrusion apparatus, should be understood to mean the application of low shear conditions such as rotation of 20 rpm.

The disadvantage of the prior art is that the processes disclosed for MGDA, apart from being complex and slow, do not work for each GLDA derivative and salt or produce solid material that is still subject to improvement in applications that require the material to be free flowable or in tableted form.

Hence, there is a need in the art for a process to prepare chelating agents in their crystalline form that gives a better particle size distribution and crystal shape, improved free flowability, strength, and morphology. Additionally there is a need for solid chelating agents that are easy to tablet, and have a sufficient speed of dissolution in an end application such as in ADW (automatic dish washing).

The present invention now provides a process to crystallize a chelating agent containing a first step of adding seeds to a saturated or supersaturated aqueous solution or dispersion of the chelating agent and a second step of milling the dispersion, and the product obtainable by the process.

The process proved to be much more efficient than the state of the art processes in the sense that it is not only faster but in many instances also provides a better particle size distribution with less extremely small particles. The crystals prepared in accordance with the present invention were found to be of an improved morphology, were more free flowable even at high humidity, and it was found possible to make tablets from them, given that they have an increased strength and yet a good dissolution rate.

Additionally, the process of the invention is favourable as no mother liquor waste stream is created, in contrast with traditional crystallization processes.

Preferably, in the process of the present invention the step of milling the dispersion is done using equipment operating at at least 1,000 rpm, more preferably at at least 10,000 rpm.

In a preferred embodiment the seeds used in the process of the invention are seeds of a chelating agent, more preferably seeds of the same chelating agent that is in the solution or dispersion and crystallized therefrom.

It should be noted that using seeds of another material than the material crystallized in the process is a process known in the art as heterogeneous nucleation. Heterogeneous nucleation can be much faster than homogeneous nucleation, but the disadvantage is that a less pure product is obtained.

In one embodiment the process of the invention contains an additional third step in which the material is at least partly dried, and optionally the material obtained from the third step is crushed or milled and sieved (to collect fractions of the right dimension), extruded, compressed, tableted or processed in any other way to be converted into the solid form that is desired.

Drying the material can for example be done by drying droplets or a thin film of the milled, seeded dispersion in an oven and is preferably done at a temperature of between 25 and 100° C.

In preferred embodiments the chelating agent is methylglycine N,N-diacetic acid or a salt thereof (MGDA), glutamic acid N,N-diacetic acid or a salt thereof (GLDA), aspartic acid N,N diacetic acid or a salt thereof (ASDA), more preferably it is GLDA or MGDA. When the chelating agent is GLDA, even more preferably it is partly acidified or fully acidified GLDA (wherein part or all of the countercations are protons).

The invention is illustrated by the Examples below

EXAMPLES

The materials used are:
Dissolvine GL-47-S (a 47 wt % solution of L-GLDA tetrasodium salt in water), ex Akzo Nobel Functional Chemicals LLC, Chicago Ill., USA.
Trilon M Powder, Trilon M Granules, Trilon M Compactate, Trilon M Liquid (40 wt % in water), which are all MGDA trisodium products ex BASF Corporation, USA.
ASDA (L-Aspartic acid N, N-diacetic acid tetrasodium salt) ex Mitsubishi Rayon Co, Ltd. Japan
Sodium Hydroxide, 50% Solution, AR®, ex Avantor
XRD Method and Equipment Used for Analysis:
The diffractograms of crystalline salts according to this invention were recorded using a Bruker-AXS D8 reflection-diffractometer using Ni filtered Cu-Kα radiation. Generator settings are 40 kV, 40 mA. A graphite monochromator was used with divergence and anti-scatter slit V20 (variable 20 mm), detector slit 0.6 mm. The measuring range was 2Θ=2.0-70.0°, step size 0.02°, time per step 6.5 seconds.

The Topas software package from Bruker was used for the diffractograms.

Example 1 Preparation of GLDA-NaH3 Solution and Seeds

To lower the pH of a GLDA-Na4 solution, Dissolvine GL-47-S, an acidification was performed using a Bi-Polar Membranes (BPM) process. In the BPM process, a bipolar membrane electrodialysis stack was used as described in WO 2008/065109. Such a unit consists of bipolar membranes and a cation exchange membrane. The sodium cations are removed through the cationic exchange membrane, while the hydrogen is added into the product stream via an electrochemical reaction. That way the solution is gradually acidified without having residual sodium cations present. This means that a "salt-free" acidification has occurred.

The experimental set-up consisted of three vessels to recycle fluids through the BPM unit. The temperature was controlled by applying heating/cooling to the jacketed reactors. The acid reactor was a 1 l stirred glass reactor and the base and electrolyte loop both used 1.5 l glass reactors without stirring. Nitrogen was passed through the electrolyte solution via a gas sparger in order to dilute the hydrogen gas produced at the cathode to far below the explosion limit.

The reactor was charged with a c. 42 wt % GLDA-Na4 solution and the recirculation of the reactor content over the BPM stack was started. Once the GLDA solution was heated to 40° C., an electric current was applied. The voltage (V) over the stack was limited to 25V and the electric current (I) was controlled manually to a maximum of 15 A. When the desired pH was reached, the current to the BPM was minimized and both the reactor and BPM contents were collected. The acidified GLDA solution was established to be a 44 wt % solution of GLDA having a pH of about 2.5.

The resulting 44.1 wt % L-GLDA aqueous solution with pH 2.5 (which corresponds to a solution containing about 1 equivalent of sodium cation per GLDA anion) were submitted to a heat treatment for 174 hours at approx. 100° C. to provide for racemization. The obtained D,L-GLDA-NaH3 solution was concentrated to a 50.2 wt % (50:50) L,D-GLDA-NaH3 aqueous solution in a rotavapor, water bath temperature 70° C. and reduced pressure (20 mbar).

An amount of 1,852 g of the above solution was charged to a 3 l jacketed glass reactor provided with an anchor stirrer. The aqueous solution was heated to 98° C. for full dissolution. Whilst being stirred the clear solution was seeded with GLDA-NaH3 crystals and cooled to 30° C. within 15 hours.

The crystal slurry was centrifuged in a horizontal Rousselet drum centrifuge to separate the mother liquor from the crystalline product.

After separation, 1,198 g of mother liquor with a concentration of 29.3% (established by way of Fe-TSV, Iron Total Sequestering Value) and 598.6 g of wet cake were obtained. The wet cake was washed twice with a small amount of water and dried under vacuum at 40° C., yielding ~450 g of dry crystals.

Example 2: Crystallization of GLDA-NaH3 Under High Shear 243.6 grams of aqueous solution GLDA-NaH3 as prepared in Example 1 above containing about 50% GLDA (assay on Fe-TSV=51.8%) were weighed into a beaker. To the sample 10 grams of GLDA-NaH3 seeds as prepared in Example 1 above were added (needle-shaped, having dimensions of 50-100 μm by 5-10 μm). Next, the seeds were milled and dispersed by using an Ultra Turrax operating for 1 minute at 24,000 rpm. (Ultra Turrax type T25 equipped with a S25n-25F mixing element).

Comparative Example 3 Crystallization of GLDA-NaH3 Under Low Shear

A sample was prepared having the composition as described in Example 2. To the sample were added needle-shaped seeds having dimensions of 50-100 μm by 5-10 μm (identical to the ones described in Example 2). Next, the dispersion of the seeds in the solution was stirred using a spatula for about 1 minute.

The dispersions obtained from Comparative Example 3 and Example 2 were submitted to a DSC analysis program starting at the same time after the components were mixed.

In this program the samples were heated from 25 to 95° C. at a heating rate of 2.5° C./min.

The material from Example 2, using the Ultra Turrax, peaked exothermically at 57° C., while for the solid obtained in Comparative Example 3 without the Ultra Turrax treatment the mixture showed a peak maximum at 70° C., which shows that the material made with the process according to the present invention crystallizes faster than material made using a state of the art process.

Example 4 Crystallization and Properties of Crystals of GLDA-NaH3

As in Example 2, 243.6 grams of aqueous solution GLDA-NaH3 containing about 50% GLDA (Fe-TSV=51.8%) were weighed into a beaker. 10 grams of crystalline GLDA-NaH3 seeds were added to the GLDA solution. High shear was applied on the mixture in accordance with Example 2.

The resulting mixture was applied as a thick film (~2.5 mm) on a polypropylene substrate and was allowed to dry at 80° C. in an oven. The resulting product could be easily broken and sieved applying a Frewitt sieve, without any difficulties concerning sieve fouling. 75% of the materials were within the specifications set (0.5-1.6 mm).

The resulting powders of Example 2 (various sieve fractions: <0.5; 0.5-0.71; 0.71-1; 1-1.6 mm) all showed free flowing behaviour even after storage at 40° C. at 75% relative humidity (RH) during 70 hrs, despite the fact that the powders showed moisture uptake up to 10%.

At ambient conditions the moisture content of the product measured using an infrared drying balance at 120° C. was about 8-12%, depending on relative humidity. The crystallinity of the sample was 49% according to XRD.

Example 5 Effect of Temperature on the Crystallization of GLDA-NaH3

The same procedure as described in Example 2 was repeated, but now the resulting mixture was divided into four fractions; two fractions were applied as thick films of ~2.5 mm and the two other fractions were partly applied as separate droplets of about 2-2.5 mm and in both cases one was allowed to dry at 80° C. and the other at room temperature.

The dried films were subsequently broken and sieved as described in Example 4. Both the sieving fractions and the granules (dried droplets) were stored at 40° C. at 75% relative humidity during 44 hrs. All samples showed free flowing behaviour, despite the fact that their final moisture contents were in between 11-13 w %.

Example 6: Influence of Concentration and Seed Content on Crystallization of GLDA-NaH3

Using similar procedures as described in Example 4, samples were prepared differing in GLDA concentration and seed content.

5 grams of each sample were dried directly after preparation using a Denver IR-60 laboratory dryer at 120° C., recording the time to get constant weight. Afterwards the crystallinity was determined using XRD.

From the results, as shown in Table 1 below, it is concluded that under these conditions, crystallization occurs within the timescale of evaporation of the water, as the crystallinity of all samples is similar considering the statistical margins of this crystallinity determination methodology (estimated at ~10%).

TABLE 1

| GLDA in solution before seeding (wt %) | seed w % on total | time to dry [minutes] | crystallinity product [XRD] |
|---|---|---|---|
| 50 | 4 | 100 | 49 |
| 50 | 20 | 44 | 53 |
| 58 | 4 | 48 | 50 |
| 64 | 4 | 30 | 48 |

Example 7 Crystallization of MGDA-Na3

48 grams of aqueous solution MGDA-Na3 containing 40% solids (Trilon M liquid, ex BASF) were weighed into a beaker. 2 grams of crystalline MGDA-Na3 (Trilon M granules ex BASF; crystallinity 43% according to XRD) were added as seeds to the MGDA solution. High shear was applied on the mixture employing an Ultraturrax for 1 min at 24,000 rpm. (Ultra Turrax type T25 equipped with a S25n-25F mixing element).

The resulting mixture was applied as a thick film (~2.5 mm) on a polypropylene substrate and was allowed to dry at 80° C. in an oven.

The crystallinity of the product was 41% according to XRD The resulting product could easily be broken and sieved, without any difficulties concerning sieve fouling. The sieve recovery of the fraction sized 0.71-2 mm was 70%.

This fraction was dried at 50° C. under vacuum overnight, prior to flow ability and moisture uptake testing. After storage for 29 hrs at 16° C. at 60% relative humidity, the sample was still free flowing, showing a moisture uptake of 16%.

Under more severe conditions, 40° C. and 75% RH, the product remained free flowing for at least 6 hours, but it lost this property after 29 hrs.

Comparative Example 8—MGDA-Na3 Commercial Product Storage and Moisture Testing

As a comparison Trilon M granulate of BASF, as used for seeding in Example 7, was subjected to the same storage conditions as the sample obtained by the process of Example 7. It was concluded that the free flowability performance of the product of the invention was at least similar.

Example 9—Influence of Concentration on Crystallization of MGDA-Na3

The process as described in Example 7 was repeated, with the only difference that the Trilon M solution used was concentrated to 50 w %.

The crystallinity of the resulting product was 45% according to XRD.

As far as moisture uptake and free flowing behaviour were concerned: within experimental error, the material performed identical to the material obtained in Example 7.

Example 10—Effect of Seeds on Crystallization of MGDA-Na3

The process as described in Example 7 was repeated, but now Trilon M powder (ex BASF; crystallinity 49%) was used as seed.

The crystallinity of the resulting product was 38% according to XRD.

Again a sieving fraction of 0.71-2 was dried at 50° C. under vacuum overnight, prior to flow ability and moisture uptake testing. After storage for 29 hrs at 16° C. at 60% relative humidity, the sample was still free flowing, showing a moisture uptake of 11%.

Under more severe conditions, 40° C. and 75% RH, the product lost its free flowing ability within one hour.

The same storage characteristics were found for the Trilon M powder (ex BASF).

Example 11 Crystallization of ASDA-Na4

48 grams of aqueous solution ASDA-Na4 (36 wt %) were weighed into a beaker. Added were 2 grams of ASDA-Na4-containing material obtained by centrifuging off a precipitate that was formed during storage of a concentrated solution, having a crystallinity of 15%, according to XRD.

High shear was applied on the mixture employing an Ultraturrax for 1 min at 24,000 rpm. (Ultra Turrax type T25 equipped with a S25n-25F mixing element).

The resulting mixture was applied as a thick film (~2.5 mm) on a polypropylene substrate and was allowed to dry at 80° C. in an oven.

The resulting product was powdered and analyzed using XRD, showing a crystallinity of 22%.

This material was used as seeding material for a subsequent experiment, following the same procedure as described above.

The resulting product was powdered and analyzed using XRD, now showing a crystallinity of 29%.

A sieving fraction of 0.71-2 mm was dried at 50° C. under vacuum overnight, prior to flow ability and moisture uptake testing. Up to 3 hrs at 16° C. at 60% relative humidity, the sample remained free flowing, showing a moisture uptake of only 12%.

Example 12 Effect of Milling Step on Morphology, Crystallinity and Dissolution Behaviour of Chelating Agent Crystals The process as described in Example 7 was used to prepare a series of products, using Trilon M Liquid that was concentrated to 50 w %.

Either 2 wt % or 20 wt % of seeds of crystalline MGDA-Na3 (Trilon M Granules ex BASF) was added, either by stirring in gently employing an eight-shaped glass stirrer rotating at 50 rpm, or by applying high shear employing an Ultraturrax for 6 minutes at 24,000 rpm. (Ultra Turrax type T25 equipped with a S25n-25F mixing element).

The crystallinities of these products were determined for the overall products and are given in Table 2. Additionally also the crystallinities were calculated of the mass not originating from the seeds added (non-seed phase).

From these data it is clear that the products obtained using the process of the present invention with milling using an Ultraturrax (using the same amount of seeds) have significantly higher crystallinities as compared to those that were mixed in via stirring.

The particle size characteristics were measured by dynamic image analyzing, according to NEN-ISO 13322-2, using a Sympatec system, from which also the specific surface area was calculated using a density of 1.72 g/ml, as measured using He-pycnometry.

No significant differences were found between the products made (see Table 2).

Sample dissolution rates of the products were determined in water at room temperature by monitoring the conductivity of the aqueous solution on addition of a fixed amount of MGDA granules.

For this test, 3.0 grams of the product were added to 300 ml of demi water in a 500 ml beaker, while the solution was stirred using a stirrer (blade: ⅔ of the diameter of the beaker) at a fixed rotation speed (150 rpm).

The results are given in Table 2, expressed in the time needed for 99% and 100% dissolution.

Surprisingly, it appears that the products made using an Ultraturrax, and thus milled with a high shear (using the same amount of seeds), show significantly faster dissolution rates, despite the fact that they show higher crystallinities.

As a reference also the characteristics of commercially available MGDA-solids, Trilon M Granules and Trilon M Compactate, are given, showing that the materials made according to the invention dissolve much faster, while they are even larger and have a smaller specific surface area.

After being dried at 50° C. during 3 days in vacuum, samples of the products were stored for 20 hours at 16° C. at a relative humidity (RH) of 60% or 6 hours at 40° C. at RH 75%, after which the moisture uptake was measured by weighing the samples. From the results, given in Table 2, it is concluded that the samples that were made using the process of the present invention with milling using an Ultraturrax (using the same amount of seeds) showed the lowest moisture uptake.

After being subjected to these conditions, all products were still free flowing, while the Trilon M Granules reference sample showed some agglomeration after storage for 6 hours at 40° C. at RH 75%, despite the fact that this reference sample showed lower moisture uptake values as compared to the samples according to the invention After being dried at 50° C. during 3 days in vacuum, 7.5 grams of samples of the products were pressed into tablets having a diameter of 25 mm, yielding a thickness of 11.1 mm, using a Herzog tablet press, type HTP 40 with a pressure of 100 kN (204 MPa) for 2 seconds, after which the diametrical breaking strength of the tablets was measured, using a Hydrospex type breaking strength tester.

From the results, given in Table 2, it is concluded that the samples that were made using the process of the present invention with milling in an Ultraturrax (using the same amount of seeds) yielded significantly stronger tablets than those obtained in a process with stirring-in of the same amount of the same seeds.

TABLE 2

| Examples (comp = comparative) Sample | Preparation conditions Ultra turrax | % seeds | particle size D10 (μm) | D50 (μm) | D90 (μm) | specific surface area (cm2/g) | crystallinity % (see NB) total measured | non-seed phase calculated | dissolution time (min) 99% | 100% | moisture uptake (w %) 20 hr 16° C. 60% RH | 6 hr 40° C. 75% RH | tablet strength kN |
|---|---|---|---|---|---|---|---|---|---|---|---|---|---|
| 12A (comp) | no | 20 | 730 | 1170 | 1630 | 32.8 | 60 | 37 | 1:15 | 1:30 | 14.6 | 27.3 | 75 |
| 12B | yes | 20 | 780 | 1230 | 1700 | 31.4 | 67 | 44 | 1:00 | 1:10 | 13.5 | 24.7 | 100 |
| 12C (comp) | no | 2 | 730 | 1160 | 1620 | 33.3 | 53 | 50 | 0:55 | 1:10 | 17.5 | 31.8 | 120 |
| 12D | yes | 2 | 750 | 1200 | 1680 | 32.2 | 61 | 58 | 0:25 | 0:40 | | | 145 |
| 12E | yes | 2 | 740 | 1140 | 1600 | 33.8 | 63 | 60 | 0:25 | 0:35 | 16 | 29.7 | 150 |
| Trilon M Granules (comp) | — | — | 790 | 1260 | 1730 | 38.8 | 75 | — | 3:40 | 5:00 | 5.1 | 16.6 | |
| Trilon M Compactate (comp) | — | — | 580 | 1050 | 1460 | 33.6 | 71 | — | 1:35 | 2:00 | | | |

NB: for these products the crystallinity was determined with renewed XRD-equipment, yielding significantly higher values for the apparent crystallinity than measured in Examples 4, 6, 7, 9. Hence the above values cannot be compared with the values mentioned in the other Examples and only with one another.

The invention claimed is:

1. Process to crystallize a chelating agent containing a step of adding seeds to a saturated or supersaturated aqueous solution or dispersion of the chelating agent and a subsequent step of milling the dispersion, wherein the step of milling the dispersion is performed using equipment operating at at least 1,000 rpm, and wherein the chelating agent is selected from the group consisting of methylglycine N,N-diacetic acid or a salt thereof (MGDA), glutamic acid N,N-diacetic acid or a salt thereof (GLDA), or aspartic acid N,N-diacetic acid or a salt thereof (ASDA).

2. Process of claim 1 wherein the step of milling the dispersion is performed using equipment operating at at least 10,000 rpm.

3. Process of claim 1 wherein the seeds are seeds of a chelating agent.

4. Process of claim 3 wherein the seeds are seeds of the chelating agent that is in the solution or dispersion.

5. Process of claim 1 containing an additional third step in which the material is at least partly dried.

6. Process of claim 5 wherein the material obtained from the third step is sieved, extruded, compressed, tableted, crushed and/or milled.

7. Process of claim 1 wherein the chelating agent is GLDA.

8. Process of claim 1 wherein the chelating agent is MGDA.

9. Product obtainable by the process of claim 1.

* * * * *